(12) United States Patent
Wang et al.

(10) Patent No.: US 11,027,121 B2
(45) Date of Patent: Jun. 8, 2021

(54) SYSTEMS, METHODS AND MEDIA FOR DIRECTIONAL COORDINATED RESET DEEP BRAIN STIMULATION

(71) Applicant: REGENTS OF THE UNIVERSITY OF MINNESOTA, Minneapolis, MN (US)

(72) Inventors: Jing Wang, Minneapolis, MN (US); Gregory F. Molnar, Minneapolis, MN (US); Jerrold L. Vitek, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 96 days.

(21) Appl. No.: 16/258,264

(22) Filed: Jan. 25, 2019

(65) Prior Publication Data
US 2019/0232049 A1 Aug. 1, 2019

Related U.S. Application Data

(60) Provisional application No. 62/622,223, filed on Jan. 26, 2018.

(51) Int. Cl.
*A61N 1/36* (2006.01)
*A61N 1/05* (2006.01)
(Continued)

(52) U.S. Cl.
CPC .......... *A61N 1/0534* (2013.01); *A61B 5/6868* (2013.01); *A61N 1/36067* (2013.01);
(Continued)

(58) Field of Classification Search
CPC .............. A61N 1/0534; A61N 1/36082; A61N 1/36067; A61N 1/08; A61N 1/36185; A61N 1/36175; A61B 5/6868
See application file for complete search history.

(56) References Cited

U.S. PATENT DOCUMENTS 7,003,352 B1    2/2006   Whitehurst
7,212,867 B2    5/2007   Van Venrooij
(Continued)

FOREIGN PATENT DOCUMENTS

DE    2015109988 B4    4/2017
WO    2005113063 A1    12/2005

OTHER PUBLICATIONS

Adamchic, I., et al., 2014. Coordinated reset neuromodulation for Parkinson's disease: Proof-of-concept study. Movement disorders, 29(13), pp. 1679-1684.
(Continued)

*Primary Examiner* — Rex R Holmes
(74) *Attorney, Agent, or Firm* — Quarles & Brady LLP

(57) ABSTRACT

In accordance with some embodiments of the disclosed subject matter, mechanisms (which can, for example, include systems, methods, and media) for directional coordinated reset deep brain stimulation are provided. In some embodiments, a method is provided, comprising: implanting a lead with segmented electrodes into an anatomical structure; selecting a first subset of the electrodes corresponding to the anatomical structure as active electrodes; causing electrical pulses at a first stimulation level to be applied at the active electrodes in a first sequence; causing electrical pulses at a second stimulation level that is lower than the first stimulation level to be applied at the active electrodes in a second sequence during a second time period; and inhibiting electrical pulses from being applied at inactive electrodes during the second time period.

20 Claims, 8 Drawing Sheets

(51) Int. Cl.
*A61B 5/00* (2006.01)
*A61N 1/08* (2006.01)
(52) U.S. Cl.
CPC ............ *A61N 1/36082* (2013.01); *A61N 1/08* (2013.01); *A61N 1/36175* (2013.01); *A61N 1/36185* (2013.01)

(56) References Cited

U.S. PATENT DOCUMENTS

| | | | |
|---|---|---|---|
| 8,032,231 | B1 | 10/2011 | Gilson |
| 8,825,167 | B2 | 9/2014 | Tass |
| 8,948,875 | B2 | 2/2015 | Paulus |
| 9,486,389 | B2 | 11/2016 | Tass |
| 9,592,389 | B2 * | 3/2017 | Moffitt ............... A61N 1/37247 |
| 2007/0135860 | A1 | 6/2007 | Tass |
| 2010/0280572 | A1 | 11/2010 | Meadows |
| 2011/0093041 | A1 * | 4/2011 | Straka ............... A61N 1/36125 607/59 |
| 2013/0245713 | A1 | 9/2013 | Tass |
| 2014/0350635 | A1 | 11/2014 | Strother |

OTHER PUBLICATIONS

Beuter, A., et al., 2014. Closed-loop cortical neuromodulation in Parkinson's disease: An alternative to deep brain stimulation?. Clinical Neurophysiology, 125(5), pp. 874-885.
Buhlmann, J., et al., 2011. Modeling of a segmented electrode for desynchronizing deep brain stimulation. Frontiers in neuroengineering, 4.
Connolly AT et al., "A Novel Lead Design for Modulation and Sensing of Deep Brain Structures," IEEE Trans. Biomed. Eng., vol. 63, No. 1, pp. 148-157, Jan. 2016.
Contarino MF et al., "Directional steering a novel approach to deep brain stimulation," Neurology, vol. 83, No. 13, pp. 1163-1169, Sep. 2014.
Deuschl, G., et al. Deep brain stimulation: postoperative issues. Mov Disord 2006; 21 Suppl 14: S219-37.
Dujardin, K., et al. Influence of chronic bilateral stimulation of the subthalamic nucleus on cognitive function in Parkinson's disease. Journal of Neurology 2001;248:603-11.
Little, S., et al. 2013. Adaptive deep brain stimulation in advanced Parkinson disease. Annals of neurology, 74(3), pp.449-457.
Lyons, MK. "Deep Brain Stimulation: Current and Future Clinical Applications," Mayo Clin. Proc., vol. 86, No. 7, pp. 562-672, Jul. 2011.
Lyskansky, B, et al., 2013. Optimal number Of stimulation contacts for coordinated reset neuromodulation. Frontiers in neuroengineering, 6.
Martens, H.C.F., et al. 2011. Spatial steering of deep brain stimulation vols. using a novel lead design. Clinical ieurophysiology, 122(3), pp. 558-566.
Pollo C. et al., "Directional deep brain stimulation: an intraoperative double-blind pilot study," Brain, vol. 137, no. 7, pp. 2015-2026, Jul. 2014.
Reich MM et al., "Short pulse width widens the therapeutic window of subthalamic neurostimulation," Ann. Clin. Trans!. NeuroL, vol. 2, No. 4, pp. 427-432, Apr. 2015.
Rodriguez-Oroz, M.C., et al. Bilateral deep brain stimulation in Parkinson's disease: a multicentre study with 4 years follow-up. Brain 2005; 128: 2240-9.
Saint-Cyr, J.A., et al. Neuropsychological consequences of chronic bilateral stimulation of the subthalamic nucleus in Parkinson's disease. Brain 2000; 123: 2091-108.
Santos, F.J., et al., 2011 Stimulation on demand: closing the loop on deep brain stimulation. Neuron, 72(2), pp. 197-198.
Steigerwald, F. et al. "Directional deep brain stimulation of the subthalamic nucleus: a pilot study using a novel neurostimulation device," Mov. Disord., vol. 31, No. 8, pp. 1240-1243, Aug. 2016.
Sun, F.T. et al., 2014. Closed-loop neurostimulation: the clinical experience. Neurotherapeutics, 11(3), pp. 553-563.
Tass, P.A., et al., 2012. Coordinated reset has sustained aftereffects in Parkinsonian monkeys. Annals of neurology, 12(5), pp. 816-820.
Timmermann, L, et al., 2013. A new rechargeable device for deep brain stimulation: a prospective patient satisfaction survey. European neurology, 69(4), pp. 193-199.
Van Nuenen, B.F., et al. Postoperative gait deterioration after bilateral subthalamic nucleus stimulation in Parkinson's disease. Mov Disord 2008; 23: 2404-6.
Waln, O. et al., 2014. Rechargeable deep brain stimulation implantable pulse generators in movement disorders: patient satisfaction and conversion parameters. Neuromodulation: Technology at the Neural Interface, 17(5), pp. 425-430.
Wang, J., et al., 2016. Coordinated reset deep brain stimulation of subthalamic nucleus produces long-lasting, dose-lependent motor improvements in the 1-methyl-4-phenyl-1, 2, 3, 6-tetrahydropyridine non-human primate model of parkinsonism. Brain stimulation, 9(4), pp. 609-617.
Fan, D., et al_ "Improving desynchronization of parkinsonian neuronal network via triplet-structure coordinated reset stimulation." Journal of theoretical biology 370 (2015): 157-170.
Popovych, O. V., et al. "Pulsatile desynchronizing delayed feedback for closed-loop deep brain stimulation." PloS ane 123 (2017): e0173363.
Popovych, O. V., et al. (2014). Control of abnormal synchronization in neurological disorders. Frontiers in neurology, 5, 268.
Tass, P. A. "A model of desynchronizing deep brain stimulation with a demand-controlled coordinated reset of neural subpopulations." Biological cybernetics 89.2 (2003): 81-88.
Tyulmankov, D., et al. (2018). Periodic flashing coordinated reset stimulation paradigm reduces sensitivity to on and Off period durations. PloS one, 13(9), e0203782.

* cited by examiner

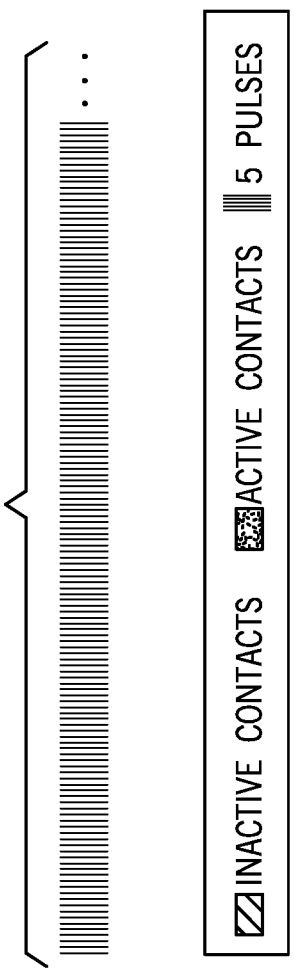
FIG. 1A
TRADITIONAL ISOCHRONAL DBS
FIG. 1B
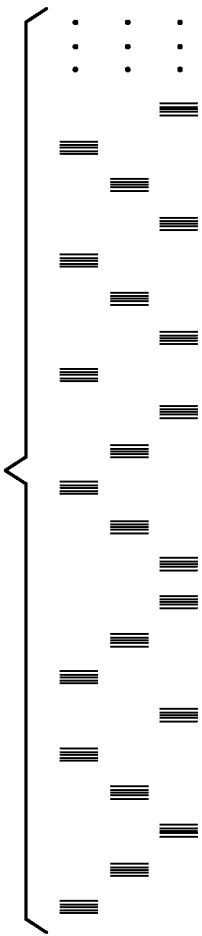
FIG. 1C
TRADITIONAL CR DBS
FIG. 1D
INACTIVE CONTACTS
ACTIVE CONTACTS
5 PULSES

SYSTEMS, METHODS AND MEDIA FOR DIRECTIONAL COORDINATED RESET DEEP BRAIN STIMULATION

CROSS-REFERENCE TO RELATED APPLICATIONS

This application is based on, claims the benefit of, and claims priority to U.S. Provisional Application No. 62/622,223, filed Jan. 26, 2018, which is hereby incorporated herein by reference in its entirety for all purposes.

STATEMENT REGARDING FEDERALLY SPONSORED RESEARCH

This invention was made with government support under NS037019, NS058945, NS077657, and NS098573 awarded by National Institutes of Health. The government has certain rights in the invention.

BACKGROUND

Deep brain stimulation (DBS) has been successfully used to treat the symptoms of Parkinson's disease (PD), but traditional isochronal DBS has not changed for decades. FIG. 1A shows an example of a lead that can be implanted into the subthalamic nucleus (STN) to provide pulses used in isochronal DBS. As shown in FIG. 1A, the lead used to deliver isochronal DBS has electrodes at various points along the lead. FIG. 1B shows an example stimulation strategy for isochronal DBS to treatment symptoms of PD. In this conventional treatment, only a single electrode is used, and pulses are continually emitted at a relatively high frequency from that single electrode into the STN. Such constant high frequency stimulation in isochronal DBS drains the device battery relatively quickly (e.g., within several years), which can require additional interventions, such as battery replacement surgeries that put patients at risk, and can have negative effects on the patients' quality of life. Additionally, traditional isochronal DBS sometimes causes side effects due to current spread, which can limit the use and/or therapeutic window for treating PD with isochronal DBS.

Some attempts have been made to develop rechargeable pulse generators, but this often requires intensive attention from patients to recharge their pulse generator every several weeks, which affects the patient's quality of life in a different way.

Closed-loop DBS, has been proposed as a solution to both the battery drain and side effect problems, but such a stimulation strategy is still undergoing the process of identifying effective biomarkers and will need long-term exploration-validation process before it can become commercially available to patients.

Accordingly, new systems, methods, and media for directional coordinated reset deep brain stimulation are desirable.

SUMMARY

In accordance with some embodiments of the disclosed subject matter, systems, methods, and media for directional coordinated reset deep brain stimulation are provided.

In accordance with some embodiments of the disclosed subject matter, a method is provided, the method comprising: implanting a lead with segmented electrodes into at least one anatomical structure of a subject; selecting a first subset of the segmented electrodes that correspond to the at least one anatomical structure as active electrodes, wherein a second subset of the segmented electrodes not selected for inclusion in the first subset are inactive electrodes; causing electrical pulses at a first stimulation level to be applied at the active electrodes in a first sequence during a first time period; inhibiting electrical pulses from being applied at the inactive electrodes during the first time period; causing electrical pulses at a second stimulation level that is lower than the first stimulation level to be applied at the active electrodes in a second sequence during a second time period; and inhibiting electrical pulses from being applied at the inactive electrodes during the second time period.

In some embodiments, the segmented electrodes comprise at least five electrodes arranged around the lead in three dimensions In some embodiments, the at least one anatomical structure comprises the subject's subthalamic nucleus.

In some embodiments, the at least one anatomical structure comprises the subject's globus pallidus.

In some embodiments, the first sequence and the second sequence are coordinated reset deep brain stimulation sequences.

In some embodiments, the method further comprises: monitoring a level of symptoms exhibited by the subject during the first time period; determining, at a second time subsequent to the first time period and preceding the second time period, that the level of symptoms is stable; in response to determining that the level of symptoms is stable, causing the electrical pulses at the second stimulation level to be applied.

In some embodiments, selecting the first subset comprises: performing a monopolar review to determine a stimulation level for each of the segmented electrodes at which side effects are caused by the stimulation; generating image data showing a relationship between the lead and the at least one anatomical structure; and determining, based on results of the monopolar review and the image data, which electrodes correspond to the at least one anatomical structure and which electrodes do not correspond to the at least one anatomical structure.

In some embodiments, the first stimulation level is between 1 milliamps (mA) and 5 mA.

In some embodiments, the second stimulation level is between 0.1 mA and 1.5 mA.

In some embodiments, the subject is a human.

In some embodiments, the method further comprises determining, for at least a first segmented electrode of the segmented electrodes, a threshold stimulation level at which side-effects attributable to the stimulation are observed.

In some embodiments, the first stimulation level is at least one-third of the threshold stimulation level.

In some embodiments, the stimulation level is no greater than the threshold stimulation level.

In some embodiments, the second stimulation level is at least one-tenth of the threshold voltage.

In some embodiments, the second stimulation level is no greater than three-tenths of the threshold voltage.

In some embodiments, a system is provided, the system comprising: a lead with segmented electrodes implanted in at least one anatomical structure of a subject; and a pulse generator that is configured to: emit electrical pulses at a first stimulation level to active electrodes of the segmented electrodes in a first sequence during a first time period, wherein the active electrodes comprise a first subset of the segmented electrodes that correspond to the at least one anatomical structure and a second subset of the segmented electrodes not included in the first subset are inactive electrodes; inhibit emission of electrical pulses to the inactive electrodes during the first time period; receive, at a second time subsequent to the first time period, an instruction from a computing device to stop emitting electrical pulses at the first stimulation level, and begin emitting electrical pulses at a second stimulation level that is lower than the first stimulation to at the active electrodes in a second sequence during a second time period; and inhibit emission of electrical pulses to the inactive electrodes during the second time period.

In some embodiments, the pulse generator is further configured to emit electrical pulses to each of the segmented electrodes during a monopolar review to determine a stimulation level for each of the segmented electrodes at which side effects are caused by the stimulation.

In some embodiments, the pulse generator is implanted in a thoracic region of the subject and is electrically connected to the lead via a cable.

In some embodiments, the instruction from the computing device is received via a wireless link between the pulse generator and the computing device.

In some embodiments, the pulse generator is further configured to, for at least a first segmented electrodes of the segmented electrodes, emit pulses of increasing intensity to determine a stimulation level for at least the first segmented electrode at which side effects are caused by the stimulation.

BRIEF DESCRIPTION OF THE DRAWINGS

Various objects, features, and advantages of the disclosed subject matter can be more fully appreciated with reference to the following detailed description of the disclosed subject matter when considered in connection with the following drawings, in which like reference numerals identify like elements.

FIG. 1A shows an example of a lead that can be implanted into the subthalamic STN to provide pulses used in isochronal DBS.

FIG. 1B shows an example stimulation strategy for isochronal DBS to treatment symptoms of PD.

FIG. 1C shows an example of electrodes used in coordinated reset DBS, which emits intermittent pulse trains from multiple electrodes of a lead.

FIG. 1D shows an example of a pattern of stimulation emissions from various electrodes on the lead.

DETAILED DESCRIPTION

In accordance with various embodiments, mechanisms (which can, for example, include systems, methods, and media) for directional coordinated reset deep brain stimulation are provided.

FIG. 1C shows an example of electrodes used in coordinated reset (CR) DBS, which emits intermittent pulse trains from multiple electrodes of a lead, and FIG. 1D shows an example of a pattern of stimulation emissions from various electrodes on the lead. As shown in FIGS. 1C and 1D, unlike in traditional isochronal DBS, multiple electrodes are used and pulses are not continuously emitted.

In some embodiments of the disclosed subject matter, a lead with segmented electrodes that are arranged in a three dimensional pattern around the exterior surface of the lead can be implanted, rather than implanting a conventional lead (which typically has only four electrode bands) used in traditional isochronal DBS. Unlike the electrodes of a conventional lead, a lead with segmented electrodes can be used to emit pulses from the lead toward a particular direction, rather than emitting a pulse around the entire circumference of the lead.

In some embodiments of the disclosed subject matter, electrodes in particular positions on the segmented lead can be activated and electrodes in other positions can be left inactive to more precisely target a particular portion of a patient's anatomy. More precise targeting can, in some cases, increase the effectiveness of a therapy, and/or provide comparable effectiveness using less energy. Additionally, more precise targeting of the patient's anatomy can reduce the amount of energy introduced into portions of the patient's anatomy that are not being targeted, which can reduce the incidence and/or severity of side effects from DBS.

In some embodiments of the disclosed subject matter, activating electrodes in particular positions on the segmented lead can facilitate directional targeting of pulses through electrodes that are in contact with the targeted portion of the patient's anatomy, while not activating other nearby electrodes that are not in contact with the targeted portion of the patient's anatomy.

In some embodiments of the disclosed subject matter, electrodes at particular positions on the segmented lead can be activated in a particular sequence(s), which can facilitate directional CR DBS. In some embodiments, a directional CR DBS therapy can be delivered by emitting short-term electrical pulse trains into brain structures (e.g. subthalamic nucleus and globus pallidus) through multiple three dimensionally spaced contacts in a fixed or varying sequence using a lead with segmented electrodes.

Figure 2B:
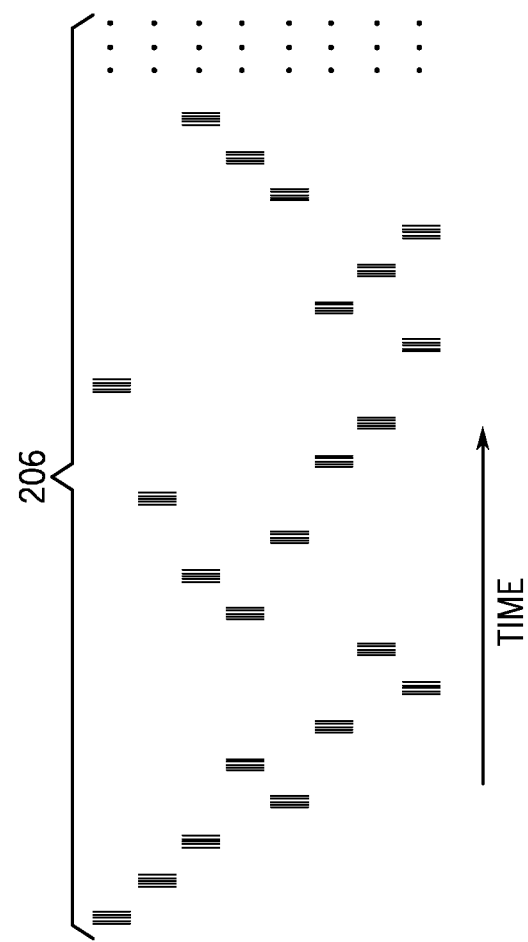
FIG. 2B shows an example of a sequence of pulses that can be emitted from electrodes to administer directional CR DBS in accordance with some embodiments of the disclosed subject matter.
Figure 2A:
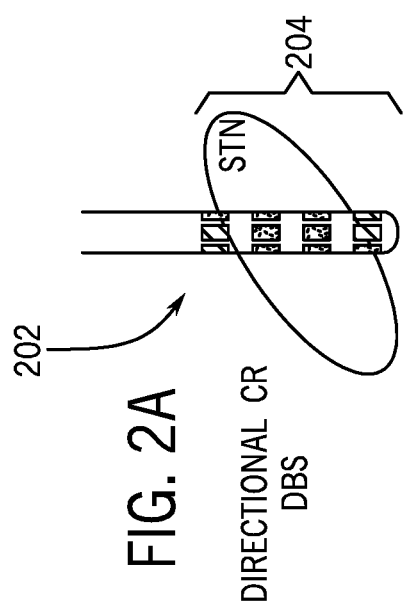
FIG. 2A shows an example of a lead having a three dimensional arrangement of segmented electrodes that can be used for directional CR DBS in accordance with some embodiments of the disclosed subject matter.

FIG. 2A shows an example of a lead 202 having a three dimensional arrangement of segmented electrodes 204 that can be used for directional CR DBS in accordance with some embodiments of the disclosed subject matter. As shown, in some embodiments, electrodes corresponding to a targeted anatomical structure (e.g., the patient's STN) can be activated, while other electrodes that are not in contact with the STN can be left inactive. FIG. 2B shows an example 206 of a sequence of pulses that can be emitted from electrodes 204 to administer directional CR DBS in accordance with some embodiments of the disclosed subject matter. In some embodiments, directional CR DBS can use many more electrodes than are used in conventional isochronal DBS and CR DBS to produce a comparable or better therapeutic effect, while reducing energy consumption (i.e., prolonging battery life), and can reduce current spread related side effects. For example, in FIG. 1C, an electrode used in CR DBS is only partially in contact with the STN, and the remainder of the electrode surface is in contact with another portion of the patient's anatomy. In such an example, when this electrode is used to emit pulses only a portion of the energy is emitted into the STN, and the remainder of the energy is introduced elsewhere, which may cause side effects related to current spread. In comparison to isochronal DBS (e.g., described above in connection with FIGS. 1A and 1B) and CR DBS (described above in connection with FIGS. 1C and 1D), directional CR DBS can increase the therapeutic window. In some embodiments, by more precisely targeting a particular portion of the patient's anatomy, high stimulation intensity pulses (e.g., higher intensity pulses that are used in CR DBS described above in connection with FIGS. 2A and 2B) can be used in an acute therapeutic treatment phase without increasing side effects, which can be followed by lower intensity stimulation to maintain the therapeutic effect.

Figure 3:
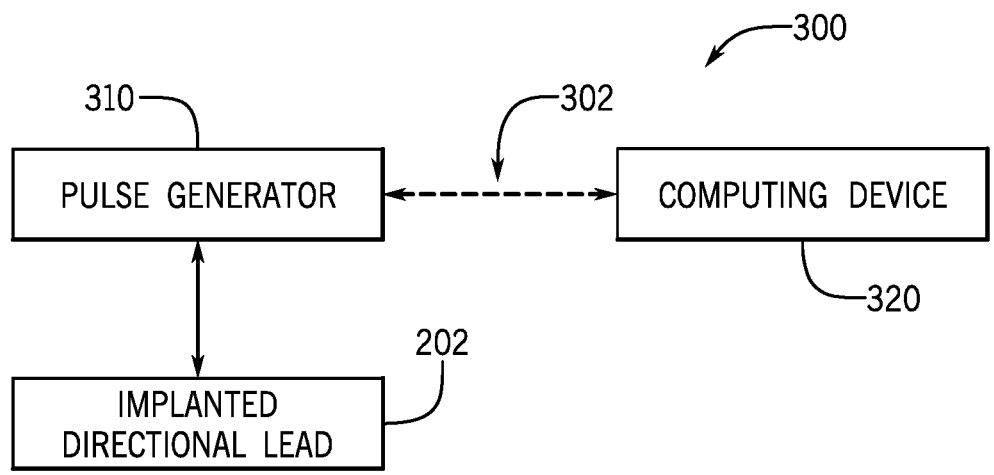
FIG. 3 shows an example of a system for directional CR DBS in accordance with some embodiments of the disclosed subject matter.

FIG. 3 shows an example 300 of a system for directional CR DBS in accordance with some embodiments of the disclosed subject matter. As shown in FIG. 3, a pulse generator 310 (e.g., an implanted pulse generator) can be interconnected with lead 202, and can be programmed (e.g., using hardware, firmware, and/or software) to produce signals to drive particular electrodes 204 in a particular sequence(s). In some embodiments, pulse generator 310 can be programmed using a computing device 320 that can communicate with pulse generator 310 via a wireless link 302. In some embodiments, any suitable wireless link can be used, such as a Bluetooth low energy link, a Z-wave link, a ZigBee link, a Wi-Fi link, a near field communication link, a proprietary radio frequency (RF) link, any other suitable wireless link, or any suitable combination of wireless links. In some embodiments, computing device 320 can be any suitable general purpose or special purpose computing device, such as a smartphone, a tablet computer, a laptop computer, a personal computer, a medical device, a remote control device, etc.

Figure 4:
FIG. 4 shows an example of a system including a lead implanted in a subject for providing directional CR DBS in accordance with some embodiments of the disclosed subject matter.

FIG. 4 shows an example 400 of a system including a lead 202 implanted in a subject for providing directional CR DBS in accordance with some embodiments of the disclosed subject matter. As shown in FIG. 4, system 400 can include pulse generator 310 that is electrically connected to one or more leads 202 implanted in the brain of the subject. In some embodiments, the subject may be a human, a non-human primate (NHP), or another animal. In some embodiments (e.g., as shown in FIG. 4), the pulse generator 310 can be contained in a separate housing that can be implanted in the thoracic region of the subject and connected to a portion of system 400 (e.g., including lead(s) 202) that is implanted in the brain, for example by a cable. Additionally or alternatively, in some embodiments, pulse generator 310 can be integrated into a portion of system 400 that is implanted in the subject's brain (not shown).

Figure 5:
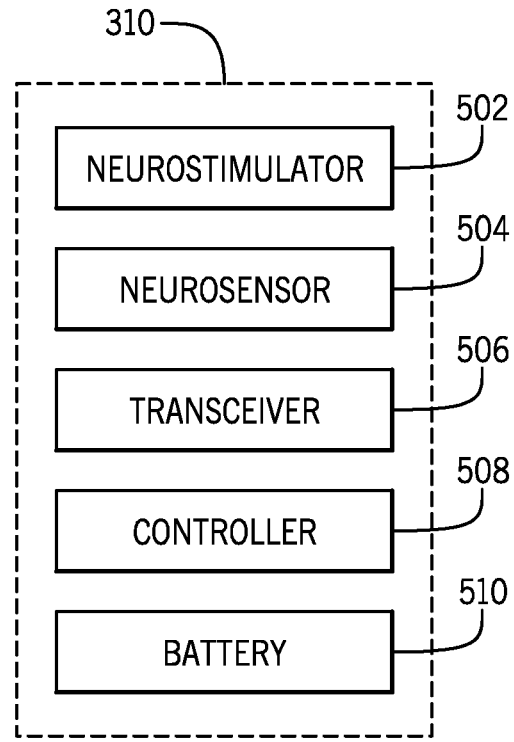
FIG. 5 shows an example of hardware that can be used to implement pulse generator in accordance with some embodiments of the disclosed subject matter.

FIG. 5 shows an example of hardware that can be used to implement pulse generator 310 in accordance with some embodiments of the disclosed subject matter. As shown in FIG. 5, in some embodiments, pulse generator 310 can include a neurostimulator 502 that is configured to send electrical pulses into the brain (e.g., via lead 202) to generate electric currents that stimulate neurons (and thus influence neural activity at a target site), and a neurosensor 504 that is configured to detect electrical signals from a target site in the brain (e.g., received via one or more electrodes 204). For example, neurosensor 504 can sense signals indicative of neural/neuronal activities of the brain through lead contacts that are not activated for stimulation. In such an example, the acquired signals indicative of neural/neuronal activities can be used directly to generate a trigger signal to start, stop and/or modify the stimulation, and/or can be processed (e.g., by an internal processor, e.g., controller 508, or external computing device, such as computing device 320) to generate a trigger signal to start, stop and/or modify the stimulation.

In some embodiments, pulse generator 310 can include a transceiver 506 that is configured to send and/or receive wireless signals (e.g., to communicate with computing device 320 as described above in connection with FIG. 3). In some embodiments, transceiver 506 can send data (e.g., sensed signals, information about operation of pulse generator 310 such as a state of a battery, a current program, etc.) to another system (e.g., computing device 320), and/or to receive data (e.g., commands, programming instructions, stimulation patterns, etc.).

In some embodiments, pulse generator 310 can include a controller 508, which can include a processor and memory for storing instructions (e.g., to be executed by the processor) for processing data (such as sensed brain activity), initiating stimulation, etc. In some embodiments, controller 508 can interact with another system (e.g., computing device 320) using via transceiver 506. In some embodiments, pulse generator 310 can include a battery 510, which can be configured to be inductively rechargeable, and can act as a source of energy for pulse generator 310.

Figure 6:
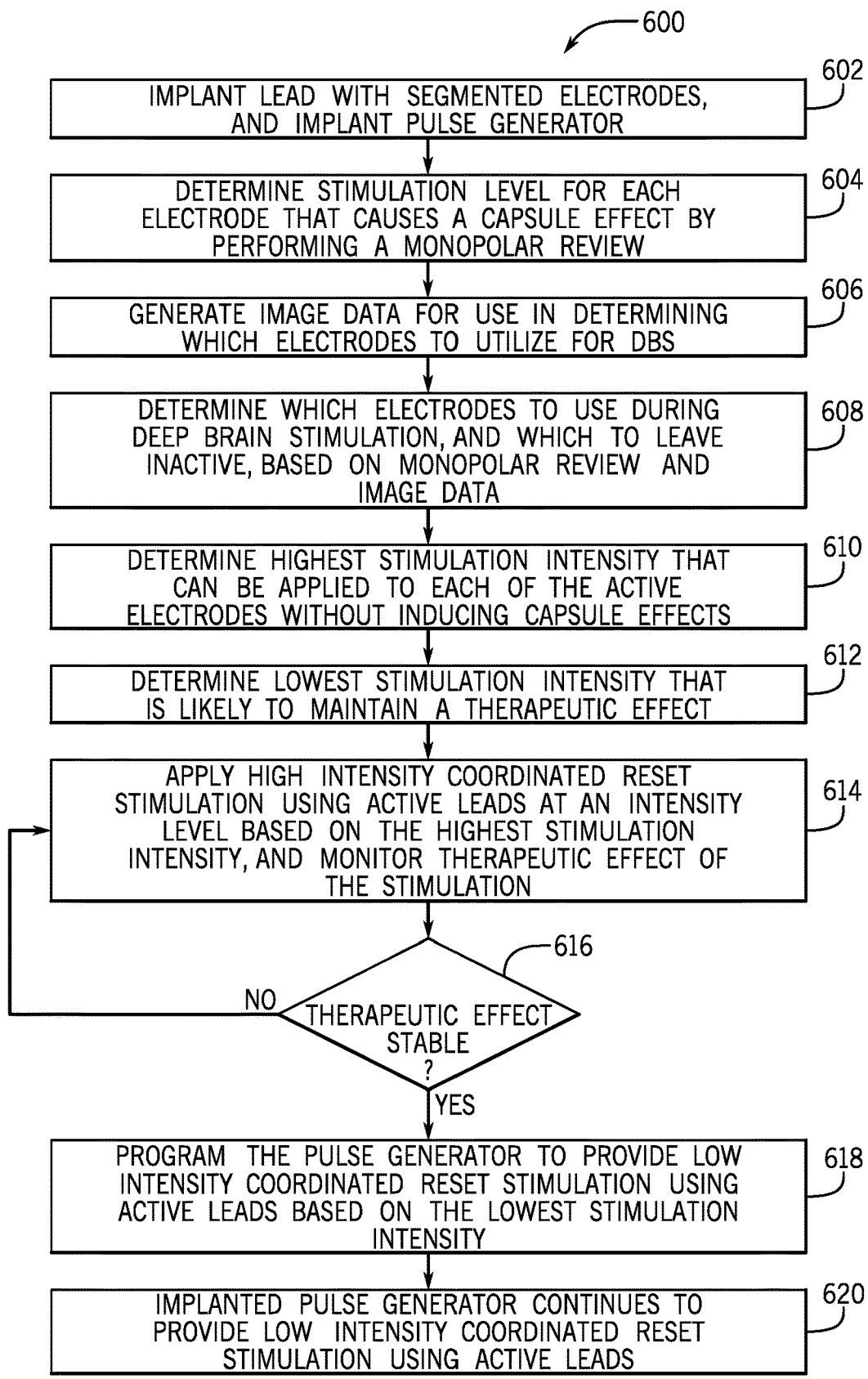
FIG. 6 shows an example 600 of a process for providing directional CR DBS in accordance with some embodiments of the disclosed subject matter.

FIG. 6 shows an example 600 of a process for providing directional CR DBS in accordance with some embodiments of the disclosed subject matter. As shown in FIG. 6, process 600 can start at 602 with surgery to implant a lead with segmented electrodes (e.g., lead 202) and a pulse generator (e.g., pulse generator 310). As described above, the lead can be implanted such that at least a portion of the electrodes are in contact with one or more anatomical features of the subject, such as the subject's STN.

At 604, process 600 can include performing a monopolar review to determine a stimulation level (e.g., a current) for each electrode at which one or more side effects are caused, such as effects due to current being introduced into the internal capsule. For example, the pulse generator can emit pulses of increasing current from a particular electrode until objective or subjective side effects are observed, such as involuntary muscle contraction, involuntary twitching, involuntary shaking, uncomfortable sensation, etc.

In some embodiments, process 600 can include recording the stimulation level (e.g., current) at which side effects were observed for each electrode.

At 606, image data showing the orientation and position of the lead implanted at 602 can be generated using any suitable technique or combination of techniques. For example, a magnetic resonance imaging (MRI) scanner can be used to generate image data that can be used to determine orientation information and/or position information of the lead by performing an Mill scan. As another example, a computed tomography (CT) scanner can be used to generate image data that can be used to determine orientation information and/or position information of the lead by performing a CT scan.

At 608, process 600 can include using the image data generated at 606 and the results of the monopolar review to determine which electrodes are likely to be within the anatomical feature that is to be stimulated (e.g., the subject's STN). For example, if stimulating a particular electrode causes capsule effects during the monopolar review at a relatively low stimulation level, this can indicate that the electrode is not within the STN. In such an example, if stimulating another electrode does not cause capsule effects until a relatively high stimulation level is used, this can indicate that the other electrode is within the STN (e.g., because energy is absorbed by tissue in the STN, and any signal that reaches the internal capsule is of relatively low intensity).

In some embodiments, information from the monopolar review can be combined with the image data to determine an orientation of each electrode with respect to the targeted portion(s) of the subject's anatomy. For example, the information from the monopolar review (i.e., the current at which capsule effects are observed) can be combined with information about the known location of the lead with respect to the subject's anatomy to determine a direction in which each electrode is facing with respect to the anatomy.

In some embodiments, at 608, process 600 can include selecting electrodes to activate during directional CR DBS based on the location and direction of each electrode, and which electrodes should remain inactive during treatment. For example, based on a combination of the image data and the monopolar review results, process 600 can determine which electrodes are likely to cause the most severe side effects, and/or which electrodes are likely to provide the greatest therapeutic effect. In some embodiments, for example, process 600 can include selecting electrodes to use during treatment by selecting electrodes that are at least in partial contact with a targeted portion of the subject's anatomy and which are likely to cause the least severe side effects. In some embodiments, the monopolar results and the image data can be used by an expert reviewer (e.g., by a radiologist, a neurologist, etc.) to determine which electrodes are located within the targeted portion of the subject's anatomy, and selections made by the expert can be provided to process 600 through user input.

At 610, process 600 can include determining a highest stimulation intensity that can be individually applied to the electrodes selected at 608 to be active electrodes without inducing side effects of greater than a threshold severity (which can be, in some cases, zero observable side effects). For example, in situations in which one or more electrodes on the implanted directional lead are to be used as the anode during treatment, stimulation can be applied at increasing intensities until side effects are observed while using the one or more electrodes as the anode. In some embodiments, results from the monopolar review can be used to determine the highest stimulation intensity (e.g., in situations in which the case of the implanted pulse generator is used as an anode). In some such embodiments, 610 can be omitted.

At 612, process 600 can include determining a lowest intensity level signal that is still likely to maintain a therapeutic effect. In some embodiments, a low intensity level can be determined by providing progressively lower intensity stimulation after an initial treatment with high intensity stimulation (e.g., as described below in connection with 614 and 616) until the effectiveness of the treatment begins to diminish below a threshold measure of effectiveness. Additionally or alternatively, in some embodiments, a low intensity level can be determined based on experimental results generated by providing high intensity treatment to a group of subjects, and providing progressively lower intensity stimulation after the initial treatment until the effectiveness of the treatment begins to diminish below a threshold measure of effectiveness. In some such embodiments, an initial lowest intensity level can be set based on the experimental results (e.g., based on the mean result, the median result, the highest result, the lowest result, etc.). In some embodiments, when a lowest intensity level is based on experimental results, the low intensity level can be adjusted after an initial application to insure that the therapeutic effectiveness of the treatment is maintained for a particular subject with the lowest stimulation level. For example, after the initial high intensity treatment, low intensity stimulation at the level determined experimentally can be applied, and adjustments can be made to the stimulation level until the effectiveness is within a threshold effectiveness of the level achieved through the high intensity treatment (e.g., within a particular range of the stabilized effectiveness observed at 616). In some embodiments, 612 can be omitted.

At 614, process 600 can include applying high intensity CR stimulation using the electrodes selected to be active electrodes. For example, as described above in connection with FIG. 2B, process 600 can cause electrodes to be activated in a particular sequence by pulse trains including five pulses each. In some embodiments, the high intensity CR stimulation can be applied at any suitable level that can induce acute therapeutic effects similar to what traditional isochronal DBS can induce relatively quickly. For example, a typical therapeutic intensity of traditional DBS is 2-5 mA (i.e. 2-5 V with 1 kiloohm (kΩ) impedance) in parkinsonian patients, and a highest intensity determined at 610 is generally expected to fall into a similar range. In a more particular example, if the highest intensity is determined as 3 mA at 610, the range of high intensity stimulation can be 1-3 mA (e.g., ⅓-full of the highest) and the range of low intensity can be 0.3 mA-0.9 mA (e.g., ¹/₁₀-310 of the highest). In some embodiments, the highest and lowest intensities used during treatment can both be customized for an individual subject. In some embodiments, as a disease progresses over time, the levels of high and low intensity levels can be adjusted to achieve a similar therapeutic effect. For example, such changes can be triggered based on feedback from the subject of the treatment. In such an example, the levels can be changed automatically based on the feedback and/or can be changed based on input provided by a physician that is treating the subject. As another example, such changes can be triggered based on changes to biomarkers determined via feedback sensed by the implanted lead and/or pulse generator (e.g., via neurosensor 504). In some embodiments, the sequence of activation can be varied at specified intervals. In some embodiments, variations in the sequence of activations can be based on experimental results from a group of subjects, and/or based on feedback (e.g., subjective and/or objective) from a particular subject (e.g., certain sequences may be more effective for some subjects than other sequences).

In some embodiments, at 614, process 600 can include monitoring the therapeutic effect of the high intensity directional CR DBS to determine whether the therapeutic effect has stabilized. For example, a clinician can record observations related to the presence or absence and/or severity of one or more symptoms exhibited by the subject, and/or can record subjective (i.e., self-reported) feedback related to the presence or absence and/or severity of various symptoms experienced by the subject. In a more particular example, as described below in connection with FIG. 7, a Unified Parkinson Disease Rating Scale (UPDRS) score can be calculated at regular and/or irregular intervals, and the score can be used as an indication of the therapeutic effectiveness of the directional CR DBS being applied. In general, during high intensity stimulation, the trend of the observed therapeutic effect can be expected to increase as a function of time, although there may be fluctuations.

Figure 8A:
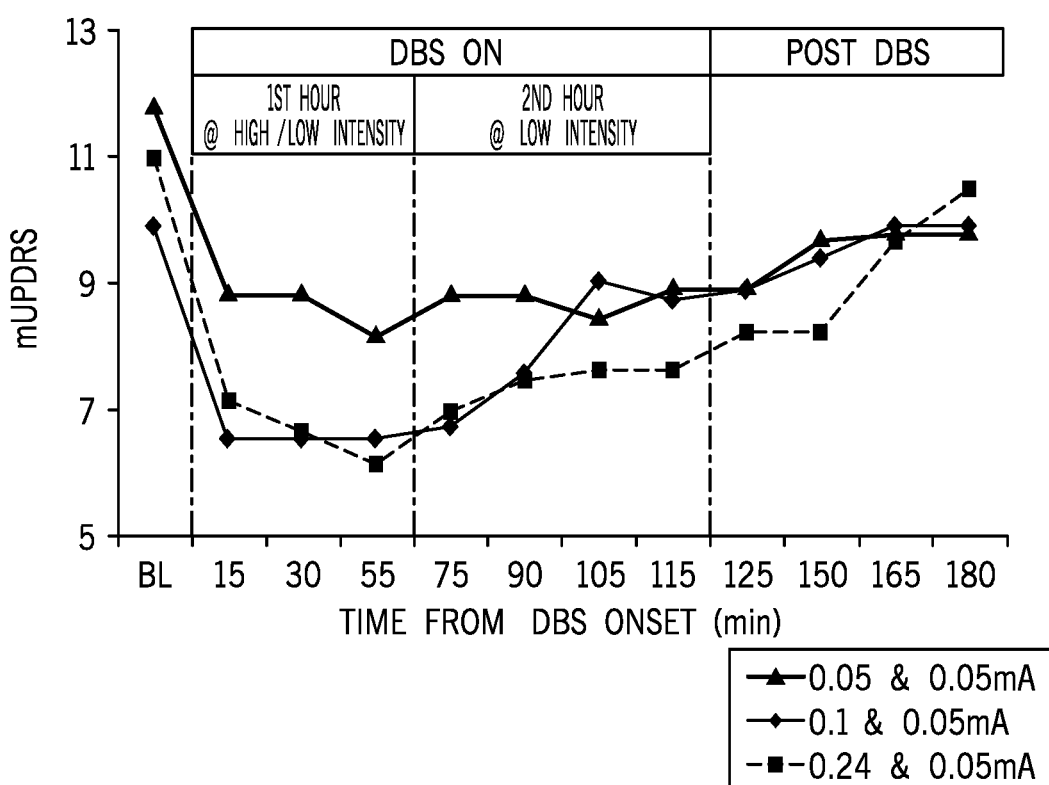
FIG. 8A shows examples of results of acute tests of CR DB S in a parkinsonian non-human primate with a regular 4-contact DBS lead measured using a version of the UPDRS modified for a non-human primate model of PD.
Figure 8B:
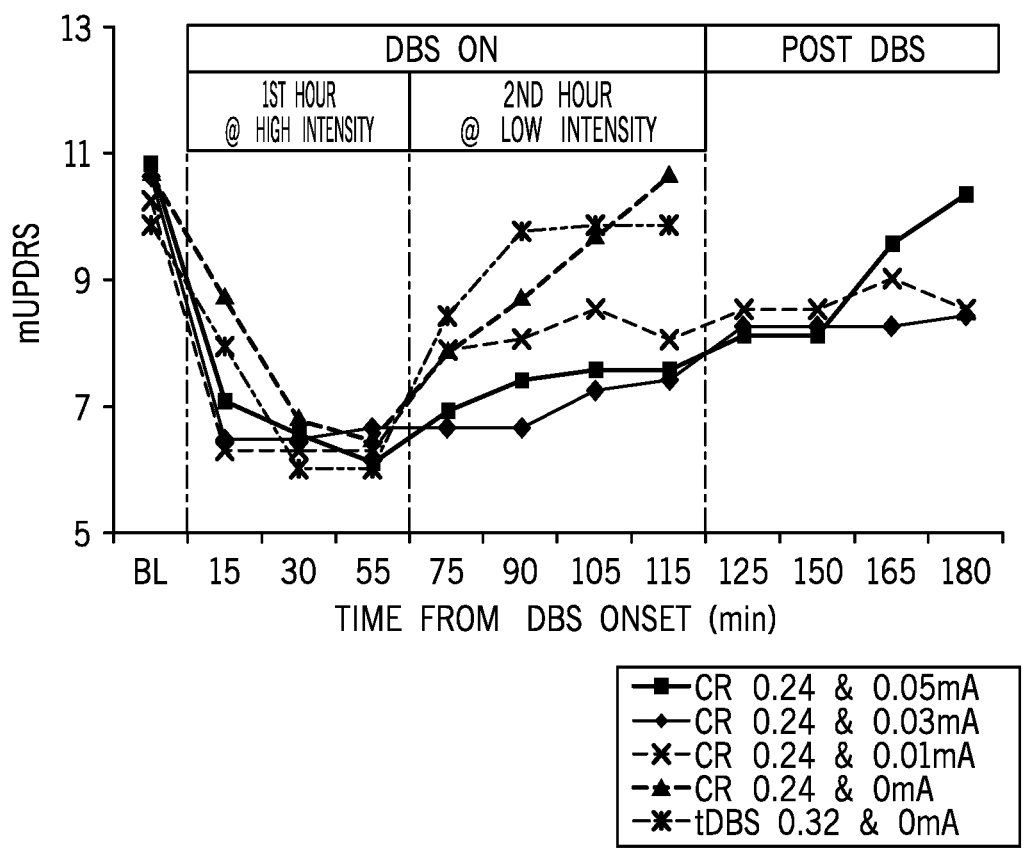
FIG. 8B shows examples of further results of acute tests of CR DBS in a parkinsonian non-human primate with a regular 4-contact DBS lead and comparison to traditional isochronal DBS (tDBS).
Figure 8C:
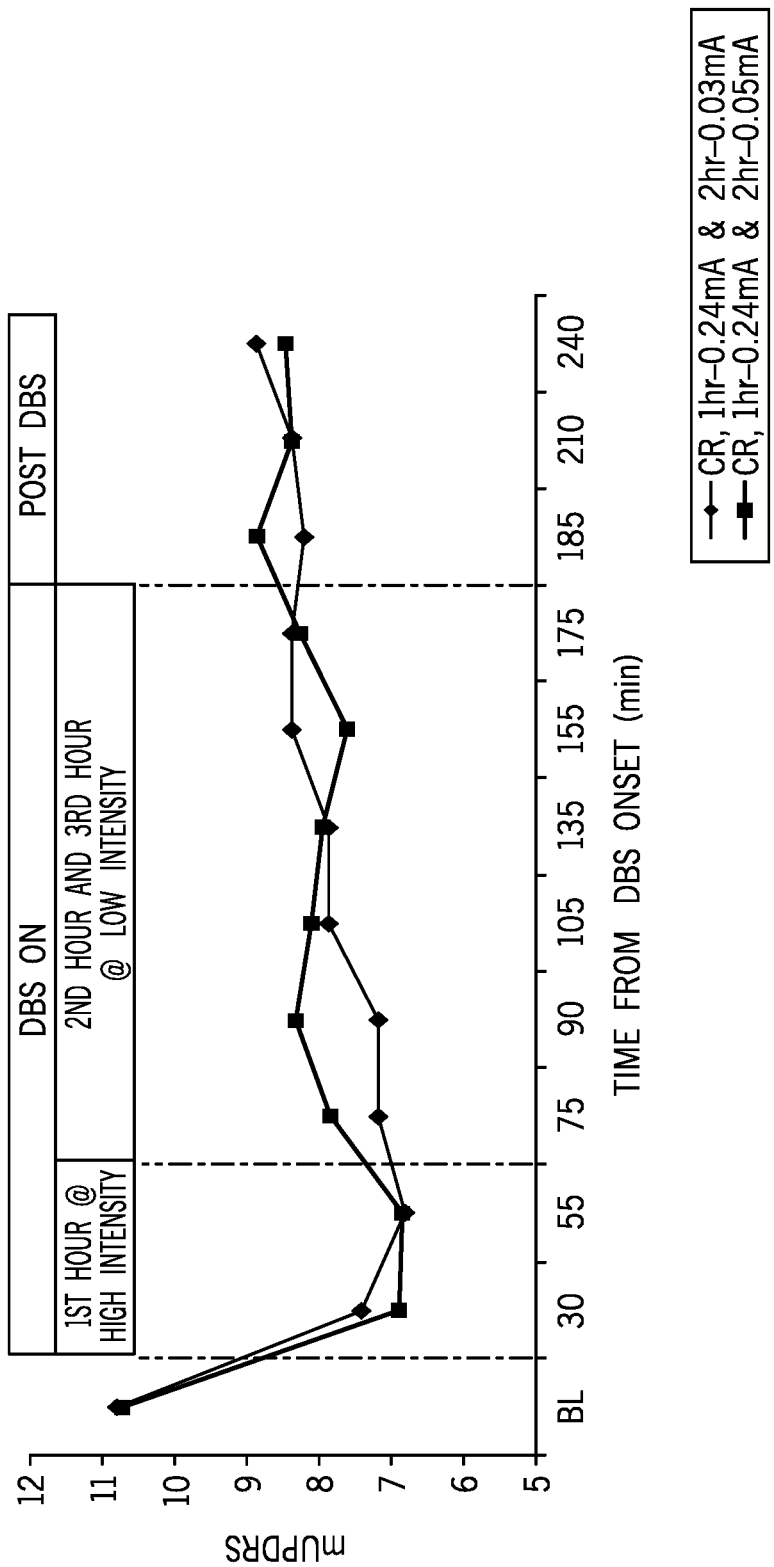
FIG. 8C shows examples of results of acute tests of CR DBS in a parkinsonian non-human primate with a regular 4-contact DB S lead with one hour of high intensity CR DBS followed by two hours of low intensity CR DBS.
Figure 8D:
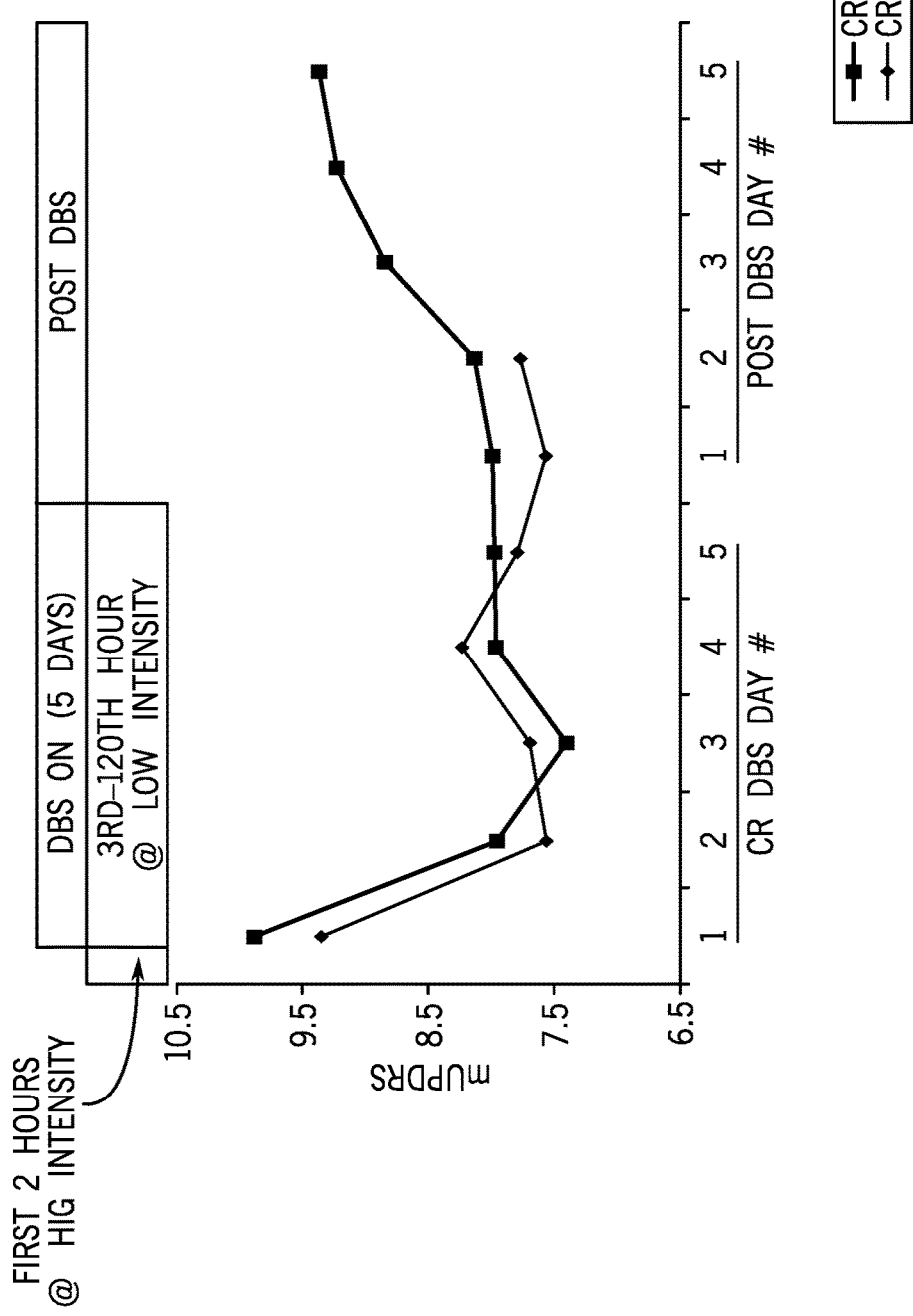
FIG. 8D shows examples of results of chronic tests of CR DBS in a parkinsonian non-human primate with a regular 4-contact DBS lead with two hours of high intensity CR DBS followed by 118 hours of low intensity CR DBS.

In some embodiments, process 600 can provide high intensity CR DBS continuously or intermittently (e.g., with or without pauses at regular and/or irregular intervals) for any suitable length of time at 614. For example, high intensity stimulation can be provided for one hour (e.g., as shown in FIGS. 8A to 8C, described below). As another example, high intensity stimulation can be provided for two hours (e.g., as shown in FIG. 8D, described below). As yet another example, the high intensity stimulation can provided for any suitable length of time until a subject's symptoms have been mitigated and have stabilized while the high intensity stimulation is provided.

At 616, process 600 can include determining whether the therapeutic effect of the high intensity CR DBS has stabilized for a particular period of time. For example, if the UPDRS scores have stopped going down and/or have started going down by a negligible amount, this can indicate that the therapeutic effect has stabilized. Additionally or alternatively, in some embodiments, process 600 can determine at 616 whether high intensity stimulation has been provided for at least a predetermined period of time (e.g., thirty minutes, one hour, two hours, etc.).

If the therapeutic effect has not stabilized ("NO" at 616) and/or the predetermined time has not elapsed, process 600 can return to 614 to continue applying high intensity directional CR DBS. Otherwise, if the therapeutic effect has stabilized ("YES" at 616) and/or the predetermined time has elapsed, process 600 can move to 618.

At 618, process 600 can include programming the pulse generator (e.g., pulse generator 310) to provide low intensity directional CR DBS using the leads selected as active leads based on the lowest effective intensity. In some embodiments, the pulse generator can be programmed using any suitable technique, such as via signals received from a computing device (e.g., computing device 320) over wireless link 302.

At 620, the implanted pulse generator can continue to provide low intensity directional CR DBS using the active leads, and the subject can continue to experience decreased symptoms while performing daily activities without as many disruptions or side effects as would be caused by traditional isochronal DBS or CR DBS. In some cases, as a disease progresses the subject may begin experiencing new symptoms, more severe symptoms, and/or a recurrence of symptoms during low intensity stimulation. In some such cases, process 600 can return to 614 to re-establish therapeutic benefits, which may include applying signals with different (e.g., higher) intensity, different sequence(s), etc.

In some embodiments, process 600 can apply low intensity stimulation continuously or intermittently (e.g., with or without pauses at regular and/or irregular intervals) for any suitable period of time. For example, low intensity stimulation can be provided for one hour (e.g., as shown in FIGS. 8A and 8B, described below). As another example, low intensity stimulation can be provided for two hours (e.g., as shown in FIG. 8C, described below). As yet another example, high intensity stimulation can be provided for a period of days (e.g., 118 hours as shown in FIG. 8D, described below), weeks, months, or longer.

Figure 7:
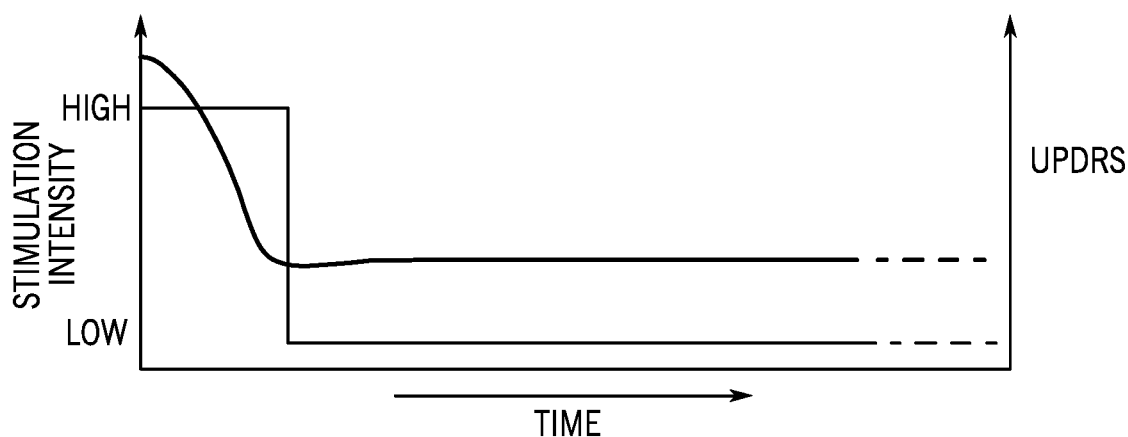
FIG. 7 shows an example of stimulation intensity and a measurement of the severity of PD symptoms that can be experienced by a subject over time as the subject is treated using directional CR DBS in accordance with some embodiments of the disclosed subject matter.

FIG. 7 shows an example of stimulation intensity and a measurement of the severity of PD symptoms that can be experienced by a subject over time as the subject is treated using directional CR DBS in accordance with some embodiments of the disclosed subject matter. As shown in FIG. 7, stimulation intensity can start at a relatively high level (e.g., as described above in connection with 614 of FIG. 6) and the UPDRS score can decrease over time during application of directional CR DBS at the relatively high level. When the UPDRS score stabilizes, the stimulation intensity can be reduced to a relatively low level while substantially maintaining the therapeutic benefits that were realized during application of high intensity CR DBS.

In some embodiments, directional CR DBS can achieve the same or better therapeutic effectiveness as other DBS treatments while using less energy. For example, because directional CR DBS uses a lower stimulation intensity (i.e., less than the energy used over the same period of time when applying traditional isochronal DBS) for all active contacts to induce acute and sustained therapeutic effect, battery life can be extended with less patient involvement. Additionally, by using a low stimulation intensity therapy, directional CR DBS can substantially maintain the therapeutic effect achieved during an acute treatment phase to further avoid patient involvement and/or battery replacement for a greater period of time than is feasible with traditional isochronal DBS.

In some embodiments, directional CR DBS can be applied using an open-loop stimulation strategy, and accordingly can be validated and approved for commercial use more quickly than more novel stimulation strategies, such as closed-loop DBS, that are not as well understood as open-loop DBS. Additionally, directional CR DBS can be adapted for further strategy development, such as exploration of different spatial and/or temporal configurations of CR and/or closed-loop CR DBS.

In some embodiments, directional CR DBS can achieve the same or better therapeutic effectiveness as other DBS treatments with a smaller battery and/or pulse generator. Because directional CR DBS can use less energy over the same period of time when compared to traditional isochronal DBS or closed-loop DBS strategies, the battery size for directional CR DBS can be reduced, which can potentially simplify surgery (e.g., by making devices with an integrated pulse generator more feasible), which has the potential to lower risks for the patient.

FIG. 8A shows examples of results of acute tests of CR DBS in a parkinsonian non-human primate with a regular 4-contact DBS lead (e.g., as described above in connection with FIGS. 2A and 2B) measured using a version of the UPDRS modified for a non-human primate model of PD (mUPDRS in FIGS. 8A-8C). In FIG. 8A, the results of two tests in which high intensity CR DBS (i.e., at 0.1 milliamps (mA) and 0.24 mA, respectively) was applied for one hour followed by low intensity CR DBS (i.e., 0.05 mA) are shown with the results of a test in which low intensity CR DBS (i.e., 0.05 mA) was applied for another hour. As shown in FIG. 8A, high intensity DBS 0.24 mA achieved the largest acute improvement and maintenance of the effect after DBS was halted.

FIG. 8B shows examples of further results of acute tests of CR DBS in a parkinsonian non-human primate with a regular 4-contact DBS lead (e.g., as described above in connection with FIGS. 2A and 2B) and comparison to traditional isochronal DBS (tDBS). As shown in FIG. 8B, different combinations of high intensity and low intensity CR DBS are compared. These results show that intensity as low as 0.03 mA may be sufficient to maintain the therapeutic effect induced by high intensity CR. As shown in FIG. 8B, when high intensity stimulation was provided for the first hour, and no stimulation was provided during the second hour (e.g., as shown in the last two lines) the therapeutic effect was not maintained as it was when low intensity stimulation was provided.

FIG. 8C shows examples of results of acute tests of CR DBS in a parkinsonian non-human primate with a regular 4-contact DBS lead (e.g., as described above in connection with FIGS. 2A and 2B) with one hour of high intensity CR DBS followed by two hours of low intensity CR DBS. Note that FIGS. 8A-8C show results for CR DBS with a conventional 4 lead DBS lead, and similar results can be expected using directional CR DBS with the potential to use a higher intensity for an acute phase due to the ability to more precisely target which electrodes to use, and/or use less energy to achieve similar results.

FIG. 8D shows examples of results of chronic tests of CR DBS in a parkinsonian non-human primate with a regular 4-contact DBS lead (e.g., as described above in connection with FIGS. 2A and 2B) with two hours of high intensity CR DBS followed by 118 hours of low intensity CR DBS. Note that FIGS. 8A-8D show results for CR DBS with a conventional 4 lead DBS lead, and similar results can be expected using directional CR DBS with the potential to use a higher intensity for an acute phase due to the ability to more precisely target which electrodes to use, and/or use less energy to achieve similar results.

Although directional CR DBS is generally described herein as being used to stimulate the STN, this is merely an example, and directional CR DBS can be used to treat other nervous system diseases in which the pathophysiology of the disease is associated with abnormal synchronization in the brain network. For example, in addition to treating the symptoms of PD, directional CR DBS can be used to treat essential tremor, dystonia, and various other neurological and psychiatric conditions.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (such as hard disks, floppy disks, etc.), optical media (such as compact discs, digital video discs, Blu-ray discs, etc.), semiconductor media (such as RAM, Flash memory, electrically programmable read only memory (EPROM), electrically erasable programmable read only memory (EEPROM), etc.), any suitable media that is not fleeting or devoid of any semblance of permanence during transmission, and/or any suitable tangible media. As another example, transitory computer readable media can include signals on networks, in wires, conductors, optical fibers, circuits, any other suitable media that is fleeting and devoid of any semblance of permanence during transmission, and/or any suitable intangible media.

It should be noted that, as used herein, the term mechanism can encompass hardware, software, firmware, or any suitable combination thereof.

It should be understood that the above described steps of the process of FIG. 6 can be executed or performed in any order or sequence not limited to the order and sequence shown and described in the figures. Also, some of the above steps of the process of FIG. 6 can be executed or performed substantially simultaneously where appropriate or in parallel to reduce latency and processing times.

Although the invention has been described and illustrated in the foregoing illustrative embodiments, it is understood that the present disclosure has been made only by way of example, and that numerous changes in the details of implementation of the invention can be made without departing from the spirit and scope of the invention, which is limited only by the claims that follow. Features of the disclosed embodiments can be combined and rearranged in various ways.

What is claimed is:

1. A method, comprising:
implanting a lead with segmented electrodes into at least one anatomical structure of a subject;
selecting a first subset of the segmented electrodes that correspond to the at least one anatomical structure as active electrodes, wherein a second subset of the segmented electrodes not selected for inclusion in the first subset are inactive electrodes;
causing electrical pulses at a first stimulation level to be applied separately to each of the active electrodes in a first coordinated reset deep brain stimulation sequence during a first time period;
inhibiting electrical pulses from being applied at the inactive electrodes during the first time period;
causing electrical pulses at a second stimulation level that is lower than the first stimulation level to be applied separately to each of the active electrodes in a second coordinated reset deep brain stimulation sequence during a second time period; and
inhibiting electrical pulses from being applied at the inactive electrodes during the second time period.

2. The method of claim 1, wherein the at least one anatomical structure comprises the subject's subthalamic nucleus.

3. The method of claim 1, wherein the at least one anatomical structure comprises the subject's globus pallidus.

4. The method of claim 1, further comprising:
monitoring a level of symptoms exhibited by the subject during the first time period;
determining, at a second time subsequent to the first time period and preceding the second time period, that the level of symptoms is stable;
in response to determining that the level of symptoms is stable, causing the electrical pulses at the second stimulation level to be applied.

5. The method of claim 1, wherein selecting the first subset comprises:
performing a monopolar review to determine a stimulation level for each of the segmented electrodes at which side effects are caused by the stimulation;
generating image data showing a relationship between the lead and the at least one anatomical structure; and determining, based on results of the monopolar review and the image data, which electrodes correspond to the at least one anatomical structure and which electrodes do not correspond to the at least one anatomical structure.

6. The method of claim 1, wherein the first stimulation level is between 1 milliamps (mA) and 5 mA.

7. The method of claim 1, wherein the second stimulation level is between 0.1 mA and 1.5 mA.

8. The method of claim 1, further comprising determining, for at least a first segmented electrode of the segmented electrodes, a threshold stimulation level at which side-effects attributable to the stimulation are observed.

9. The method of claim 8, wherein the first stimulation level is between one-third of the threshold stimulation level and the threshold stimulation level.

10. The method of claim 8, wherein the second stimulation level is between one-tenth of the threshold stimulation level and two-tenths of the threshold stimulation level.

11. A system, comprising:
  a lead with segmented electrodes implanted in at least one anatomical structure of a subject; and
  a pulse generator that is configured to:
    emit electrical pulses at a first stimulation level separately to each of a plurality of active electrodes of the segmented electrodes in a first coordinated reset deep brain stimulation sequence during a first time period, wherein the plurality of active electrodes comprise a first subset of the segmented electrodes that correspond to the at least one anatomical structure and a second subset of the segmented electrodes not included in the first subset are inactive electrodes;
    inhibit emission of electrical pulses to the inactive electrodes during the first time period;
    receive, at a second time subsequent to the first time period, an instruction from a computing device to stop emitting electrical pulses at the first stimulation level, and begin emitting electrical pulses at a second stimulation level that is lower than the first stimulation separately to each of the plurality of active electrodes in a second coordinated reset deep brain stimulation sequence during a second time period; and
    inhibit emission of electrical pulses to the inactive electrodes during the second time period.

12. The system of claim 11, wherein the at least one anatomical structure comprises the subject's subthalamic nucleus.

13. The system of claim 11, wherein the pulse generator is further configured to emit electrical pulses to each of the segmented electrodes during a monopolar review to determine a stimulation level for each of the segmented electrodes at which side effects are caused by the stimulation.

14. The system of claim 11, wherein the first stimulation level is between 1 milliamps (mA) and 5 mA.

15. The system of claim 11, wherein the second stimulation level is between 0.1 mA and 1.5 mA.

16. The system of claim 11, wherein the pulse generator is implanted in a thoracic region of the subject and is electrically connected to the lead via a cable.

17. The system of claim 11, wherein the instruction from the computing device is received via a wireless link between the pulse generator and the computing device.

18. The system of claim 11, wherein the pulse generator is further configured to, for at least a first segmented electrodes of the segmented electrodes, emit pulses of increasing intensity to determine a stimulation level for at least the first segmented electrode at which side effects are caused by the stimulation.

19. The system of claim 18, wherein the first stimulation level is between one-third of the threshold stimulation level and the threshold stimulation level.

20. The system of claim 18, wherein the second stimulation level is between one-tenth of the threshold stimulation level and two-tenths of the threshold stimulation level.

* * * * *

UNITED STATES PATENT AND TRADEMARK OFFICE
CERTIFICATE OF CORRECTION

PATENT NO. : 11,027,121 B2  Page 1 of 1
APPLICATION NO. : 16/258264
DATED : June 8, 2021
INVENTOR(S) : Jing Wang et al.

It is certified that error appears in the above-identified patent and that said Letters Patent is hereby corrected as shown below:

In the Specification

Column 4, Line 7, "DB S" should be --DBS--.

Column 4, Line 16, "DB S" should be --DBS--.

Column 7, Line 12, "Mill" should be --MRI--.

Signed and Sealed this
Twenty-seventh Day of July, 2021

Drew Hirshfeld
*Performing the Functions and Duties of the*
*Under Secretary of Commerce for Intellectual Property and*
*Director of the United States Patent and Trademark Office*